United States Patent
Toia et al.

(10) Patent No.: US 8,396,547 B2
(45) Date of Patent: Mar. 12, 2013

(54) GETTER DEVICE FOR ACTIVE SYSTEMS FOR THE TRANSDERMAL RELEASE OF DRUGS

(75) Inventors: Luca Toia, Carnago VA (IT); Cristian Landoni, Novara NO (IT)

(73) Assignee: Saes Getters S.p.A., Lainate MI (IT)

( * ) Notice: Subject to any disclaimer, the term of this patent is extended or adjusted under 35 U.S.C. 154(b) by 298 days.

(21) Appl. No.: 11/995,432

(22) PCT Filed: Jun. 30, 2006

(86) PCT No.: PCT/IT2006/000507
§ 371 (c)(1),
(2), (4) Date: Jan. 11, 2008

(87) PCT Pub. No.: WO2007/010576
PCT Pub. Date: Jan. 25, 2007

(65) Prior Publication Data
US 2008/0255497 A1 Oct. 16, 2008

(30) Foreign Application Priority Data
Jul. 15, 2005 (IT) .............................. MI2005A1356

(51) Int. Cl.
*A61N 1/30* (2006.01)
(52) U.S. Cl. ........................................ 604/20; 424/448
(58) Field of Classification Search .................... 604/20, 604/501, 890.1, 892.1
See application file for complete search history.

(56) References Cited

U.S. PATENT DOCUMENTS

| | | | | |
|---|---|---|---|---|
| 4,817,594 A | * | 4/1989 | Juhasz | 602/42 |
| 4,821,733 A | * | 4/1989 | Peck | 600/361 |
| 5,698,217 A | * | 12/1997 | Wilking | 424/448 |
| 5,827,359 A | * | 10/1998 | Dobson et al. | 96/147 |
| 6,185,452 B1 | * | 2/2001 | Schulman et al. | 604/20 |
| 2002/0173743 A1 | * | 11/2002 | Tapper | 604/20 |
| 2004/0047901 A1 | * | 3/2004 | Beier et al. | 424/449 |
| 2005/0004618 A1 | * | 1/2005 | Scott et al. | 607/45 |
| 2005/0075263 A1 | | 4/2005 | Gomez | |
| 2005/0075623 A1 | * | 4/2005 | Riddle et al. | 604/501 |

FOREIGN PATENT DOCUMENTS

| | | |
|---|---|---|
| EP | 0 811 390 A1 | 12/1997 |
| EP | 1090616 | 10/2000 |
| EP | 1 090 616 A2 | 4/2001 |
| EP | 1 115 168 A1 | 7/2001 |
| IL | 188741 | 2/2012 |
| JP | 63-231882 | 9/1988 |
| JP | 04-051766 | 4/1992 |

(Continued)

OTHER PUBLICATIONS

Notification before Examination for Israeli Patent Application No. 188741 filed on Jun. 30, 2006 in the name of Saes Getters S.p.A.

(Continued)

*Primary Examiner* — Tatyana Zalukaeva
*Assistant Examiner* — Brandy C Scott
(74) *Attorney, Agent, or Firm* — Steinfl & Bruno, LLP

(57) ABSTRACT

A getter system (20) is provided for the sorption of organic molecules on the inside of active systems (30) for the transdermal release of drugs. The getter system is suitable to avoid the corrosion of electrical parts of these systems, caused by these organic molecules in the presence of water.

14 Claims, 2 Drawing Sheets

FOREIGN PATENT DOCUMENTS

| JP | 11-511677 | 12/1999 |
|---|---|---|
| JP | 2003-077549 | 3/2003 |
| WO | 98/28478 A1 | 7/1998 |
| WO | 99/25625 A1 | 5/1999 |
| WO | 2007/010576 | 1/2007 |

OTHER PUBLICATIONS

Office Action for Israeli Patent Application No. 188741 filed on Jun. 30, 2006 in the name of Saes Getters S.p.A.

Response to Office Action mailed on Jul. 4, 2011 for Israeli Patent Application No. 188741 filed on Jun. 30, 2006 in the name of Saes Getters S.p.A.

Notice of Reasons for Rejection mailed on Oct. 4, 2011 for Japanese Patent Application No. 2008-521039 filed Jun. 30, 2006 filed in the name of Saes Getters S.p.A.

Notice of Reasons for Rejection mailed on Feb. 7, 2012 for Japanese Patent Application No. 2008-521039 filed Jun. 30, 2006 filed in the name of Saes Getters S.p.A.

PCT International Search Report mailed on Oct. 19, 2006 for PCT Application No. PCT/IT2006/000507 filed on Jun. 30, 2006 in the name of Saes Getters S.p.A.

PCT Written Opinion mailed on Oct. 19, 2006 for PCT Application No. PCT/IT2006/000507 filed on Jun. 30, 2006 in the name of Saes Getters S.p.A.

\* cited by examiner

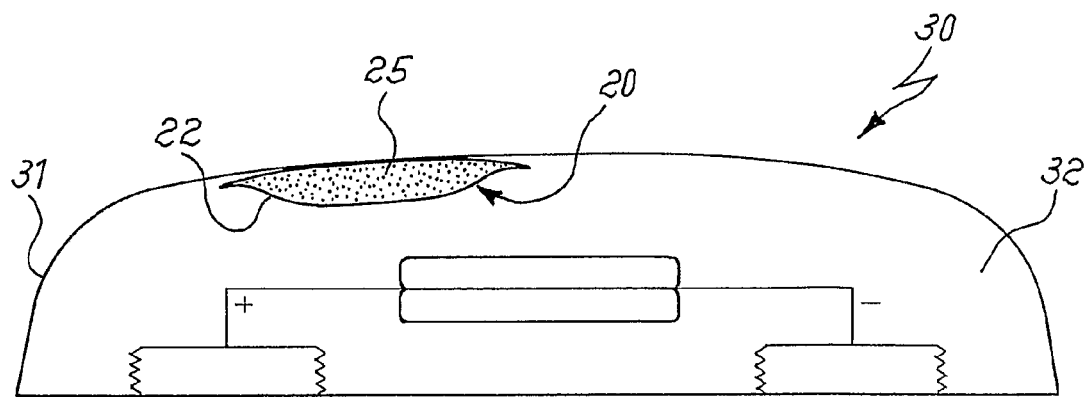
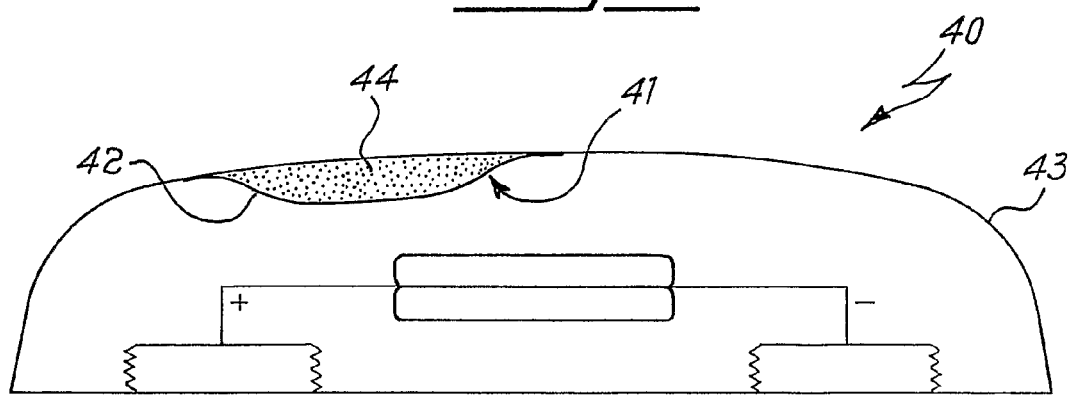

GETTER DEVICE FOR ACTIVE SYSTEMS FOR THE TRANSDERMAL RELEASE OF DRUGS

CROSS-REFERENCE TO RELATED APPLICATIONS

This application is a Section 371 of International Application No. PCT/IT2006/000507, filed Jun. 30, 2006, which was published in the English language on Jan. 25, 2007, under International Publication No. WO 2007/010576 A1 and the disclosure of which is incorporated herein by reference.

BACKGROUND OF THE INVENTION

The present invention relates to a getter device for active systems for the transdermal release of drugs.

Systems for the transdermal release of drugs are used in the treatment of conditions, dysfunctions or diseases requiring a regular administration of drugs to a patient, such as post-operative aches, cardiovascular diseases or diabetes. These systems essentially consist of an envelope of polymeric material having on the inside the drug to be dispensed, generally in form of suspension in a gel. A portion of the envelope surface is made of a plastic material permeable to the drug. By causing this portion of the envelope to adhere to the patient's skin (e.g., on an arm), the drug is released onto and absorbed by the skin itself, then entering the blood stream.

The first transdermal systems, appeared at the beginning of 1990s, were of the so-called passive type, wherein the drug release was determined only by the velocity of absorption by the skin. These systems have a number of drawbacks, such as the fact that it is impossible to control the drug flow (and consequently its dosing over a unit of time), as well as that it is impossible to have intermittent administrations, only for prefixed durations of time and at prefixed intervals or only upon the patient's request, which on the contrary are the more appropriate administration modes in some cases.

Therefore, more recently, active systems for releasing drugs have been introduced which are based on ionophoresis, i.e., transportation of drugs in ionic form under the effect of electrical fields. An example of this kind of apparatus is schematically shown in FIG. 1. The system T is formed of an envelope P on the inside of which there is a gel H, in which the drug is dispersed. The system also comprises a microcomputer MC, being fed by a battery B that controls the polarity of two electrodes E and E'. The battery is preferably of the lithium type. When the electrodes are not fed, there is no flow towards the skin of ions corresponding to the drug, whereas when the microcomputer feeds the electrodes, ions $F^+$, corresponding to the drug, are forced to pass through the permeable parts of the envelope towards the skin. At the second electrode there is a passage of sodium ions $Na^+$ from the skin towards a container of saline solution, in order to keep the system neutral. The Fig. refers to the case where the ion corresponding to the drug is positively charged, but the system operates with ions with negative charge $F^-$ as well, in this case being balanced by the transportation of chlorine ions $Cl^-$ from the skin to the transdermal system. The microcomputer can be programmed for a timed release of the drug. The system can also comprise a push-bottom for releasing the drug upon the patient's request (not shown in the drawing).

The problem that has been observed with active transdermal systems is that the battery releases dimethoxyethane (also indicated in the following as DME), an essential component of the process of manufacturing the batteries, which is kept partly trapped inside thereof. This compound together with water, always present in these systems, forms corrosive solutions attacking the electrical parts, thus leading in time to the loss of functionality of the system. Other acid components can be released by the polymeric material itself forming the envelope. For example, a material commonly employed to make the envelope is Surlyn® (Surlyn® is a registered trademark of the Du Pont company of Wilmington, Del., USA), a mixture of ethylene/(meth)acrylic acid copolymer, other polymers, such as polyesters or nylon, and including charges of metallic salts. It has been observed that in the working conditions of transdermal systems, Surlyn® releases small quantities of acetic acid, which in any case contributes to the problem of corrosion of the electrical parts.

The problem of organic components being released by batteries in general (not necessarily in field of the present application) is known, e.g., from European patent application publication EP 1 115 168 A1. According to the teaching of this document, the problem can be solved by introducing on the inside of the battery a material for the sorption of organic compounds, such as silica, alumina, titanium oxide, or porous solid particles of polymers. The problem of this solution is that, first of all, battery manufacturing is complicated. In addition, in order not to have a continuous removal of organic components of the electrolyte, such as DME or the like (necessary for the battery operation), the sorbing material in this case is coated with a layer of material impermeable to the organic compound, which material dissolves only as a consequence of malfunctions of the battery which cause its overheating. Thereby, this solution is inefficient to absorb the DME quantities, however small, which are released by the battery under normal operating conditions, i.e., when the temperature of the battery does not exceed the foreseen values. Consequently, a battery of the type described in the mentioned patent application would not solve the above-described problems of active systems for transdermal release of drugs.

BRIEF SUMMARY OF THE INVENTION

An object of the present invention is to provide a solution to the above-mentioned problems.

This and other objects are achieved according to the present invention with a getter device for active systems for the transdermal release of drugs, comprising activated charcoals and at least a first wall, permeable to organic molecules, but capable of retaining solid particles, the first wall being coupled to a second wall capable of retaining solid particles, so that the assembly resulting by the connection of the first wall and the second wall is suitable to contain the activated charcoals.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3 is a schematic representation of a system similar to that of FIG. 1, including a getter device of the invention shown in FIG. 2; and FIG. 4 is a schematic representation of a transdermal system comprising an alternative embodiment of a getter device of the invention.

DETAILED DESCRIPTION OF THE INVENTION

Figure 1:
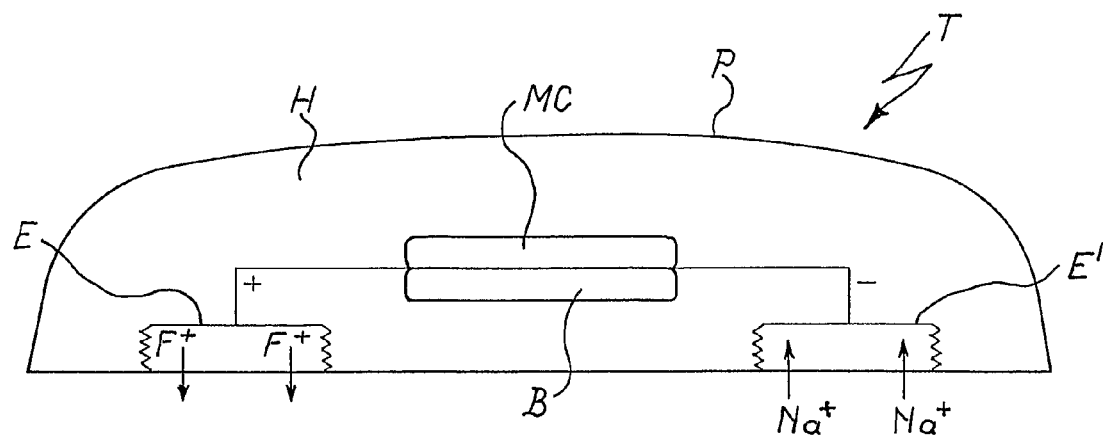
FIG. 1 is a schematic representation of an active system for the transdermal release of drugs according to the prior art.

FIG. 1 has been already described with reference to the prior art in the Background section above.

Figure 2:
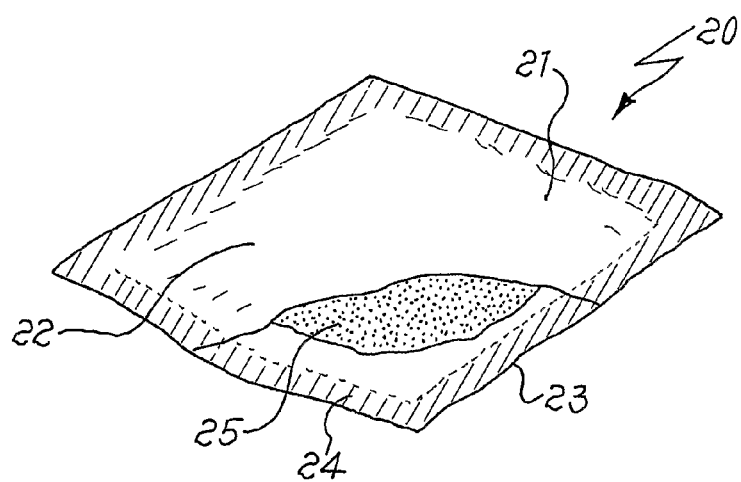
FIG. 2 is a schematic, partially broken-away, perspective view of one embodiment of a getter device according to the present invention.

FIG. 2 shows a first possible embodiment of a getter device according to the invention. In this embodiment the device 20 comprises an envelope 21 formed of two sheets, the first one forming the first wall 22 permeable to the organic molecules but capable of retaining particles, the second one forming the second wall 23. The two sheets are mutually coupled at the peripheral zone 24 identified by the hatched area in the FIG. 2. The activated charcoals 25 are contained within the envelope. The two sheets can be continuous polymers having a sufficient permeability with respect to small organic molecules, such as dimethoxyethane or organic acids. Preferably, however, the sheets are made with a fabric, either normal or nonwoven, of polymeric fibers. For example, it is possible to use two sheets of nonwoven fabric made with polyolefin fibers (e.g., polyethylene or polypropylene), of polyesters, such as PET, or Teflon® (Teflon® is a registered trademark of the Du Pont company). The joining of the two walls 22 and 23 in zone 24 can be obtained by glues, but preferably is obtained by heat sealing. In the latter case, to favor their welding, the two sheets are preferably made of the same material.

In an alternative embodiment (not shown in the drawings), the envelope can be formed by joining a wall permeable to the organic molecules (e.g., a sheet similar to that of wall 22, as described above) and an impermeable wall, which can be a polymeric sheet of greater thickness than that of the permeable wall or a metallic sheet, such as of aluminum. In the latter case, the impermeable wall can be formed as a cup for housing the activated charcoals.

The activated charcoals useful for the present invention are the simple ones, not impregnated with additional substances. Charcoals of this type are sold, e.g., by the C*Chem company of Lafayette, Colo., USA, under the trademark Chemsorb 1000, or by the Chemviron Carbon company of Feluy, Belgium.

The amount of activated charcoals contained in the device depends upon the required life length of the transdermal system. For example, in order to ensure to the system a life of about 3 years, including the storage time between production and actual use, it has been observed with accelerated tests that at least 50 mg of activated charcoals are required.

The getter device of the invention can be located at any position inside the envelope of the transdermal system. However, the getter device is preferably fixed to the system envelope in a region remote from those parts where the ionic flow occurs from and toward the skin. FIG. 3 shows this preferred embodiment. The transdermal system 30 comprises an envelope 31 having on the inside gel 32 in which the drug is suspended, and electronic parts, as already described with reference to FIG. 1. In addition, the system includes the getter device 20, adhering to a portion of the internal surface of envelope 31 remote from the electrodes for the ionic species transportation, with at least wall 22, permeable to organic molecules, in contact with gel 32.

In view of manufacturing the system of FIG. 3, the getter device 20 is caused to adhere to the internal wall of envelope 31, preferably by heat sealing. In the latter case, at least the sheet designed to be fixed to the internal wall of the envelope, among those forming envelope 21, is made of a material chosen for the function of heat sealability with envelope 31. For example, if envelope 31 is made with a Surlyn® containing a copolymer with ethylene, the sheet of wall 23 can be made with a polyolefin.

In an alternative embodiment of the transdermal system, shown in FIG. 4, the getter device is not a discrete component, but is integrated in the system itself and is manufactured in a production step of the final system. In this embodiment of the transdermal system 40, the getter device 41 comprises a first wall 42, permeable to organic molecules but capable of retaining solid particles, the perimeter of which is directly fixed to the internal surface of the envelope 43 of system 40, such that in this case a portion of envelope 43 also forms the second wall of the getter device. In the pocket thus formed, there are housed the activated charcoals 44.

This second embodiment can be manufactured, for example, by placing powders of activated charcoals on a small portion of the polymeric sheet intended to form the envelope 43 and by fixing the perimeter of a sheet designed to form wall 42, having the required features described above, along a closed line completely encircling the area where the activated charcoals are present. Alternatively, it is possible to use a support (e.g., metallic) having in its top portion a recess of similar shape and size as those of the final getter device; to lay and cause the sheet, which will form wall 42, to adhere within the recess; to pour the desired quantity of activated charcoals onto the sheet, in an area corresponding to the recess; to cause the peripheral portion of the sheet to adhere to a polymeric sheet intended to form the envelope 43, fixing the two sheets by gluing or heat sealing; and finally, to remove the support. Other sequences of operations for obtaining the system shown in FIG. 4 will be clear to those skilled in the art. The envelope 43 with an "integrated" getter device thus obtained is then employed for the subsequent steps of production of the transdermal system. Also in this case, the coupling between the sheet intended to form wall 42 and envelope 43 is preferably performed by heat sealing, and consequently the materials for envelope 43 and the sheet forming wall 42 will be chosen in a way suitable to the purpose, as described above.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An active transdermal system for the release of drugs, the system comprising a control device powered by a battery and a getter device, the getter device comprising particles of activated charcoal and at least a first wall, the first wall being permeable to organic molecules but capable of retaining solid particles, the first wall being coupled to a second wall also capable of retaining solid particles, such that an assembly resulting by the coupling of the first wall and the second wall contains the particles of activated charcoal, wherein the control device is capable of controlling transdermal drug flow from the system through ionic flow from and towards the system, wherein the getter device is located in a region of the system remote from where the ionic flow occurs, and wherein the drugs to be released are in direct contact with the getter device.

2. The active transdermal system according to claim 1, wherein the first wall comprises a continuous polymeric sheet.

3. The active transdermal system according to claim 1, wherein the first wall comprises a fabric of polymeric fibers, the fabric being woven or non-woven.

4. The active transdermal system according to claim 1, wherein the first wall comprises a material selected from sheets or fibers, the sheets or fibers being selected from polyolefin, polyester and Teflon.

5. The active transdermal system according to claim 1, wherein the first and second wall are mutually coupled by heat sealing.

6. The active transdermal system according to claim 1, wherein the second wall of the getter device is selected from a continuous polymeric sheet, woven fabrics, and non-woven fabrics.

7. The active transdermal system according to claim 1, wherein the second wall of the getter device is a portion of an internal surface of an envelope of the system itself.

8. The active transdermal system of claim 1, wherein the getter device is remote from the control device, the battery, and any interconnection between the control device and the battery.

9. An active transdermal system for release of drugs comprising:
   an electrode adapted to release drugs from the system;
   a control device to control the polarity of the electrode;
   a battery to power the control device;
   a drug dispersed within the system, the drug adapted to be transdermally released from the system through control exerted by the control device on the electrode; and
   a getter device in contact with the drug, permeable to the drug and capable of retaining particles released by the battery, the getter device being located inside the system remote from the electrode and outside a path from the control device to the electrode.

10. The active transdermal system of claim 9, wherein the control device is a microcomputer.

11. The active transdermal system of claim 9, wherein the system forms an envelope and wherein the getter device is in touch with an internal surface of the envelope and not in touch with the control device, the battery or the electrode.

12. The active transdermal system of claim 11, wherein the getter device is remote from an interconnection between the control device and the electrode.

13. The active transdermal system of claim 9, wherein the getter device contains particles of activated charcoal.

14. The active transdermal system of claim 13, wherein the getter device comprises a first wall and a second wall coupled with the first wall, and wherein the particles of activated charcoal are located between the first wall and the second wall.

\* \* \* \* \*